US007867770B2

(12) United States Patent
Premasiri

(10) Patent No.: US 7,867,770 B2
(45) Date of Patent: Jan. 11, 2011

(54) NANOSTRUCTURED SUBSTRATE FOR SURFACE ENHANCED RAMAN SCATTERING

(75) Inventor: W. Ranjith Premasiri, Weymouth, MA (US)

(73) Assignee: Trustees of Boston University, Boston, MA (US)

( * ) Notice: Subject to any disclaimer, the term of this patent is extended or adjusted under 35 U.S.C. 154(b) by 802 days.

(21) Appl. No.: 11/792,013

(22) PCT Filed: Dec. 5, 2005

(86) PCT No.: PCT/US2005/043793

§ 371 (c)(1),
(2), (4) Date: May 31, 2007

(87) PCT Pub. No.: WO2006/060734

PCT Pub. Date: Jun. 8, 2006

(65) Prior Publication Data

US 2008/0096005 A1 Apr. 24, 2008

Related U.S. Application Data

(60) Provisional application No. 60/632,930, filed on Dec. 3, 2004, provisional application No. 60/633,735, filed on Dec. 6, 2004.

(51) Int. Cl.
*G01N 21/65* (2006.01)

(52) U.S. Cl. ...................... 436/66; 356/301; 422/82.05; 422/82.09; 436/86; 436/94; 436/164; 436/166; 436/171; 436/501; 436/514; 436/525

(58) Field of Classification Search ................. 356/301; 422/82.05, 82.09; 436/66, 86, 94, 164, 166, 436/171, 501, 514, 525
See application file for complete search history.

(56) References Cited

U.S. PATENT DOCUMENTS 6,180,415 B1 1/2001 Schultz et al. .............. 436/518

(Continued)

FOREIGN PATENT DOCUMENTS

WO WO 03/010511 A2 2/2003

OTHER PUBLICATIONS

Pol, V. G. et al, Chemistry of Materials 2003, 15, 1111-1118.*

(Continued)

*Primary Examiner*—Arlen Soderquist
(74) *Attorney, Agent, or Firm*—Weingarten, Schurgin, Gagnebin & Lebovici LLP

(57) ABSTRACT

The present invention provides a nanostructured substrate for SERS. A substrate of the invention comprises a surface featuring substantially monodisperse-sized metal nanoparticles disposed thereon. Preferably, the substrate surface provides for SERS and spectra therefrom. For example, a nanostructured substrate of the invention can be used to reproducibly and reliably detect or identify pathogens, molecules or combinations thereof. In one embodiment, a nanostructured substrate of the invention comprises a surface featuring metal nanoparticles substantially aggregated in clusters thereon. Exemplary metal nanoparticles disposed on the substrate surface can be silver, copper, gold or combinations thereof. Metal nanoparticles disposed on a substrate surface can also be substantially spheroidal comprising diameters in a range from about 40 to 120 nm. The invention also provides methods for syntheses and uses of a nanostructured substrate comprising a surface featuring substantially monodisperse-sized metal nanoparticles.

19 Claims, 12 Drawing Sheets

U.S. PATENT DOCUMENTS

| | | | | |
|---|---|---|---|---|
| 6,242,264 | B1 | 6/2001 | Natan et al. | 436/171 |
| 6,514,767 | B1 | 2/2003 | Natan | 436/166 |
| 6,624,886 | B2 | 9/2003 | Natan et al. | 356/301 |
| 6,778,316 | B2 | 8/2004 | Halas et al. | 359/296 |

OTHER PUBLICATIONS

Jasiorski, M. et al, "Surface-enhanced Raman spectra of substances adsorbed on Ag0 clusters deposited on SiO2 submicron spheres prepared by the sol-gel method" Optical Materials May 6, 2004, vol. 26, pp. 145-149.

Akbarian, F. et al, "Porous sol-gel silicates containing gold particles as matrixes for surface-enhanced Raman spectroscopy" Journal of Raman Spectroscopy 1996, vol. 27, pp. 775-783.

Lee, Y. -H. et al, "Silver-doped sol-gel films as the substrate for surface-enhanced Raman scattering" Journal of Raman Spectroscopy 1997, vol. 28, pp. 635-639.

Volkan, M. et al, "A new surface-enhanced Raman scattering substrate based on silver nanoparticles in sol-gel" Journal of Raman Spectroscopy 1999, vol. 30, pp. 1057-1065.

Premasiri, W.R. et al, "Determination of cyanide in waste water by low-resolution surface-enhanced Raman spectroscopy on sol-gel substrates" Journal of Raman Spectroscopy 2001, vol. 32, pp. 919-922.

Guzelian, A.A. et al, "SERS of whole-cell bacteria and trace levels of biological molecules" SPIE 2002, vol. 4577, pp. 182-192.

Alexander, T.A. et al, "Near-infrared surface-enhanced Raman scattering (SERS) mediated identification of single optically trapped bacterial spores" SPIE 2003, vol. 5085, pp. 91-100.

Grow, A.E. et al, "New biochip technology for label-free detection of pathogens and their toxins" Journal of Microbiological Methods 2003, vol. 53, pp. 221-233.

Bao, L. et al, "Silver-doped sol-gel film as a surface-enhanced Raman scattering substrate for detection of uranyl and neptunyl ions" Analytical Chemistry Dec. 1, 2003, vol. 75, No. 23, pp. 6614-6620.

* cited by examiner

NANOSTRUCTURED SUBSTRATE FOR SURFACE ENHANCED RAMAN SCATTERING

CROSS REFERENCE TO RELATED APPLICATIONS

This application claims the priority of U.S. Provisional Application No. 60/632,930 filed Dec. 3, 2004 and entitled, SEEDED DEPOSITION OF METAL NANO-CLUSTERS USING NANO-PARTICLES ON A SOLID MATRIX, and U.S. Provisional Application No. 60/633,735 filed Dec. 6, 2004 and entitled, SEEDED DEPOSITION OF METAL NANO-CLUSTERS USING NANO-PARTICLES ON A SOLID MATRIX, which are hereby incorporated by reference herein.

BACKGROUND OF THE INVENTION

The fields of nanoscience and nanotechnology generally concern the synthesis, fabrication and use of nanoparticles and nanostructures at atomic, molecular and supramolecular levels. The nanosize of these particles and structures offers potential for research and applications across various scientific disciplines such as materials science, engineering, physics, chemistry, spectroscopy, computer science, microscopy and biology. For example, surfaces or substrates employing nanostructures can be used to enhance Raman scattering by many orders of magnitude, an effect often referred to as surface enhanced Raman scattering (SERS).

SERS is a common spectroscopic technique that can be used for detecting and identifying biological molecules. Typically, unique vibrational signatures or fingerprints can be observed for biological molecules via SERS. In aqueous media, the ability to rapidly produce such a vibrational signature for a biological molecule lacking visible chromophores demonstrates the potential of SERS as a valuable analytical and structural spectroscopic technique. SERS can be particularly useful for the detection and identification of biological molecules present in a sample at low concentrations. Recent SERS applications and developments have also extended toward the detection and identification of bacterial and viral pathogens. To date, conventional surfaces or substrates for SERS have been largely unsuccessful in reproducibly and reliably detecting and identifying such pathogens.

SUMMARY OF THE INVENTION

The present invention provides a nanostructured substrate for SERS. In one embodiment, a substrate of the invention comprises a surface featuring substantially monodisperse-sized metal nanoparticles disposed thereon. Preferably, the substrate surface provides for SERS and spectra therefrom generally referred to as SERS spectra. For example, a nanostructured substrate of the invention can be used to reproducibly and reliably detect or identify pathogens, molecules or combinations thereof. A substrate of the invention overcomes the shortcomings of conventional surfaces or substrates for SERS such as those described above.

A substrate of the invention can comprise monodisperse-sized metal nanoparticles substantially aggregated in clusters. Exemplary clusters of monodisperse-sized metal nanoparticles can comprise from about 2 to 25 nanoparticles. In one embodiment, nanoparticles for a substrate of the invention are substantially spheroidal comprising diameters in a range from about 40 to 120 nanometers (nm). Preferably, metal nanoparticles can comprise diameters in a range from about 80 to 120 nanometers nm. Metal nanoparticles for a substrate of the invention can also comprise silver, gold, copper or combinations thereof. A nanostructured substrate of the invention can comprise silicon, aluminum, titanium or combinations thereof.

Preferably, a substrate of the invention provides for SERS of an entity. Exemplary entities can include spores, pathogens, fluids, cells, amino acids, biological materials, molecules, nucleic acids, tissue samples, viruses, bacteria, inorganic materials, serums, vegetative samples, germinating samples, sputum, human blood, bronchoalveolar lavage fluid, cerebral spinal fluid or combinations thereof. In one embodiment, a nanostructured substrate can comprise an entity substantially disposed on a surface thereof. The substrate surface also comprises substantially monodisperse-sized metal nanoparticles. The entity of the substrate can be in contact with one or more substantially monodisperse-sized metal nanoparticles.

The invention also provides a method of detecting or identifying an entity via a nanostructured substrate comprising monodisperse-sized metal nanoparticles disposed on a surface thereof. In one embodiment, the method comprises providing a nanostructured substrate of the invention. The method also comprises disposing an entity substantially on the surface of the substrate. Preferably, the method comprises performing Raman microscopy of the entity on the substrate surface. Exemplary Raman microscopy yields at least one SERS spectrum of the entity. The method of the invention can also comprise detecting or identifying the entity based on a SERS spectrum.

For example, a method of the invention can detect or identify an entity by a comparison of the SERS spectrum to a reference vibrational signature. In one embodiment, a reference vibrational signature for an entity can be part of a vibrational signature library. Preferably, a vibrational signature library comprises SERS spectra for a plurality of entities. An exemplary vibrational signature library can be produced or developed using a nanostructured substrate of the invention for SERS. A vibrational signature library of the invention can comprise at least one reference vibrational signature.

In another embodiment, the invention provides a vibrational signature for an entity. Preferably, the vibrational signature is obtained by providing a nanostructured substrate comprising monodisperse-sized metal nanoparticles. An entity can be disposed on the surface of the substrate for performing Raman microscopy thereof. Exemplary Raman microscopy yields at least one SERS spectrum, which comprises a vibrational signature unique to the entity. For example, the vibrational signature can be a reference vibrational signature for detecting or identifying the entity. The vibrational signature can also be part of a vibrational signature library comprising SERS spectra for a plurality of entities such as pathogens, molecules or combinations thereof.

The invention also provides a method for detecting or identifying an entity via SERS spectra. In one embodiment, the method comprises providing a nanostructured substrate featuring monodisperse-sized metal nanoparticles disposed on a surface thereof. The method also comprises disposing an entity substantially on the surface of the substrate. Preferably, the method comprises performing Raman microscopy of the entity on the substrate surface to yield at least one SERS spectrum of the entity. Preferably, the entity disposed on the surface of the substrate is in contact with one or more substantially monodisperse-sized metal nanoparticles.

The method of the invention also comprises comparing a SERS spectrum of the entity to spectra of a vibrational signature library. As described above, an exemplary vibrational signature library can comprise SERS spectra for a plurality of entities. For example, the vibrational signature library can comprise SERS spectra of pathogens such as bacteria or viruses. Preferably, the method of the invention comprises detecting or identifying an entity based on a comparison of at least one SERS spectrum thereof to spectra of the vibrational signature library.

The invention also provides methods for syntheses of a nanostructured substrate comprising substantially monodisperse-sized metal nanoparticles. In one embodiment, a method for synthesis of a nanostructured substrate for SERS comprises hydrolyzing a solution comprising metal precursors. Moreover, the method comprises reducing the metal precursors in a matrix for subsequent growth of substantially monodisperse-sized metal nanoparticles on a surface of the substrate, which forms from the matrix. The method also comprises further reducing the metal precursors to grow the metal nanoparticles on the substrate surface.

Preferably, the metal precursors are rapidly reduced in the matrix during a first reduction step. The metal precursors are then slowly reduced during a second reduction step to grow substantially monodisperse-sized metal nanoparticles on the surface of the substrate. In one embodiment, the first reduction step can also be characterized by seed growth in the matrix. These seeds provide preferential growth sites for the subsequent growth of monodisperse-sized metal nanoparticles on a surface of the substrate. The second reduction step can also aid in the grow of the seeds within the matrix.

The invention also provides methods for uses of a nanostructured substrate comprising substantially monodisperse-sized metal nanoparticles. In one embodiment, a method for using a nanostructured substrate of the invention comprises obtaining SERS spectra therefrom. Preferably, the SERS spectra comprise a vibrational signature unique to at least one entity such as a pathogen, molecule or combination thereof. The vibrational signature of the spectra can also be a used to detect and identify the entity. For example, the entity can be detected or identified in any suitable media such as an aqueous media.

DESCRIPTION OF THE DRAWINGS

Other features and advantages of the invention may also be apparent from the following detailed description thereof, taken in conjunction with the accompanying drawings of which:

FIG. 13(*b*) shows SERS spectra of the supernatant from culture medium containing bovine viral diarrhea virus particles and a SERS spectrum for the corresponding culture medium supernatant of non-infected cells obtained via a nanostructured substrate of the invention.

DEFINITIONS

Unless otherwise stated, the following definitions provide meaning and examples to terms used herein. Such definitions are also intended to encompass any meaning that may be contemplated by a person of ordinary skill within the art.

The terms “monodisperse” or “monodisperse-sized” and derivations thereof such as substantially monodisperse-sized generally refer to substantially uniformly or homogeneously proportioned or sized particles such as metal nanoparticles. For example, metal nanoparticles for a nanostructured substrate of the invention can be physically distinguishable from particles within conventional surfaces or substrates for SERS as these nanoparticles are substantially uniformly or homogeneously proportioned or sized.

DETAILED DESCRIPTION OF THE INVENTION

The present invention provides a nanostructured substrate for SERS. A substrate of the invention comprises a surface featuring substantially monodisperse-sized metal nanoparticles disposed thereon. In one embodiment, a nanostructured substrate of the invention comprises a surface featuring metal nanoparticles substantially aggregated in clusters. Exemplary metal nanoparticles disposed on the substrate surface can be silver, gold, copper or combinations thereof. Preferably, metal nanoparticles disposed on a substrate surface can be substantially spheroidal. A substrate surface can also comprise silicon dioxide, aluminum oxide, titanium dioxide or combinations thereof.

The invention also provides methods for syntheses or uses of a nanostructured substrate comprising monodisperse-sized metal nanoparticles disposed on a surface thereof. In one embodiment, a method of the invention can be performed to obtain a nanostructured substrate comprising monodisperse-sized metal nanoparticles. For example, the method can comprise growing substantially monodisperse-sized metal nanoparticles on the substrate surface. Preferably, a method of the invention is also performed to detect or identify an entity. The method can comprise performing Raman microscopy of the entity to produce a SERS spectrum thereof.

Figure 1:
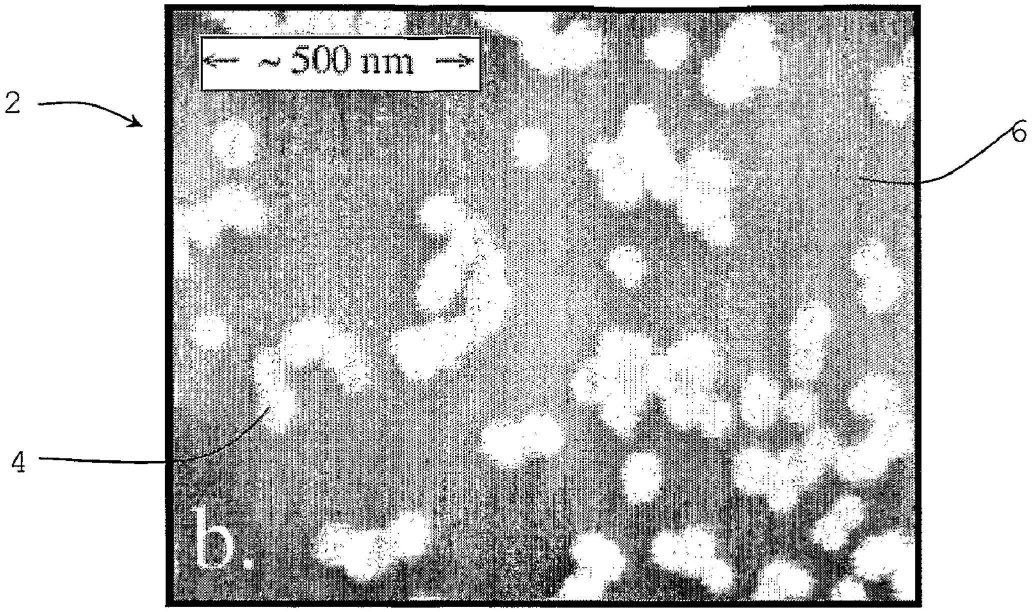
FIG. 1 shows a scanning electron microscopy (SEM) image of an exemplary nanostructured substrate of the invention.

FIG. 1 shows an SEM image of an exemplary nanostructured substrate of the invention. As shown, the substrate 2 comprises substantially monodisperse-sized gold nanoparticles 4 disposed on a surface 6 thereof. The substrate 2 and surface 6 of FIG. 1 comprise silicon dioxide. The monodisperse-sized gold nanoparticles 4 are substantially spheroidal comprising diameters in a range from about 40 to 120 nm. FIG. 1 shows the gold nanoparticles 4 as substantially aggregated in clusters. Exemplary clusters for a substrate of the invention can comprise from about 2 to 25 metal nanoparticles.

Figure 2:
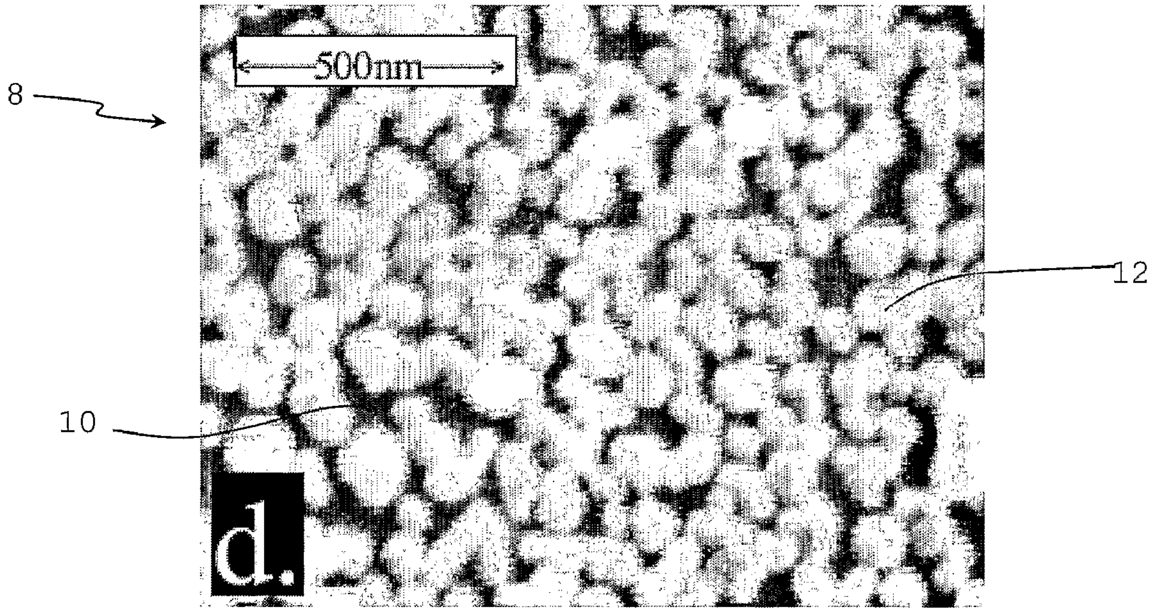
FIG. 2 shows an SEM image of an exemplary nanostructured substrate of the invention.

FIG. 2 shows an SEM image of an exemplary nanostructured substrate of the invention. As shown, the substrate 8 comprises substantially monodisperse-sized silver nanoparticles 10 disposed on a surface 12 thereof. The substrate 8 and surface 10 of FIG. 2 comprise silicon dioxide. Exemplary substrates of the invention can comprise silicon dioxide, aluminum oxide, titanium dioxide or combinations thereof. The monodisperse-sized silver nanoparticles 10 in FIG. 2 are substantially aggregated in clusters. Exemplary metal nanoparticles for a substrate of the invention can comprise silver, copper, gold or combinations thereof.

The surface topology or morphology of exemplary substrates such as shown in FIGS. 1 and 2 can affect SERS and spectra therefrom. For example, the substantially monodisperse-sized gold nanoparticles in FIG. 1 can feature a lower gold nanoparticle density on or along the substrate surface than the silver nanoparticles of FIG. 2. In one embodiment, monodisperse-sized metal nanoparticles such as silver can substantially or entirely cover or coat a nanostructured substrate surface. Exemplary monodisperse-sized silver nanoparticles for a substrate of the invention can be substantially spheroidal having diameters in a range from about 40 to 120 nm.

SERS and spectra therefrom via a substrate of the invention can be comparable for different types of nanoparticles, although vibrational signatures of an entity are generally metal dependent. Vibrational signature metal dependence for a substrate can be related to different surface topologies or morphologies. In addition, vibrational signature metal dependence can also be related to the chemical properties of the nanoparticles disposed on the substrate surface. Preferably, a substrate of the invention can provide for SERS spectra of bacterial or viral pathogens. A nanostructured substrate can also yield SERS spectra of chemical or biological molecules. For example, a substrate of the invention provides for a Raman cross-sectional enhancement of about $5\times10^7$ for glycine at an excitation of 785 nm.

Figure 3:
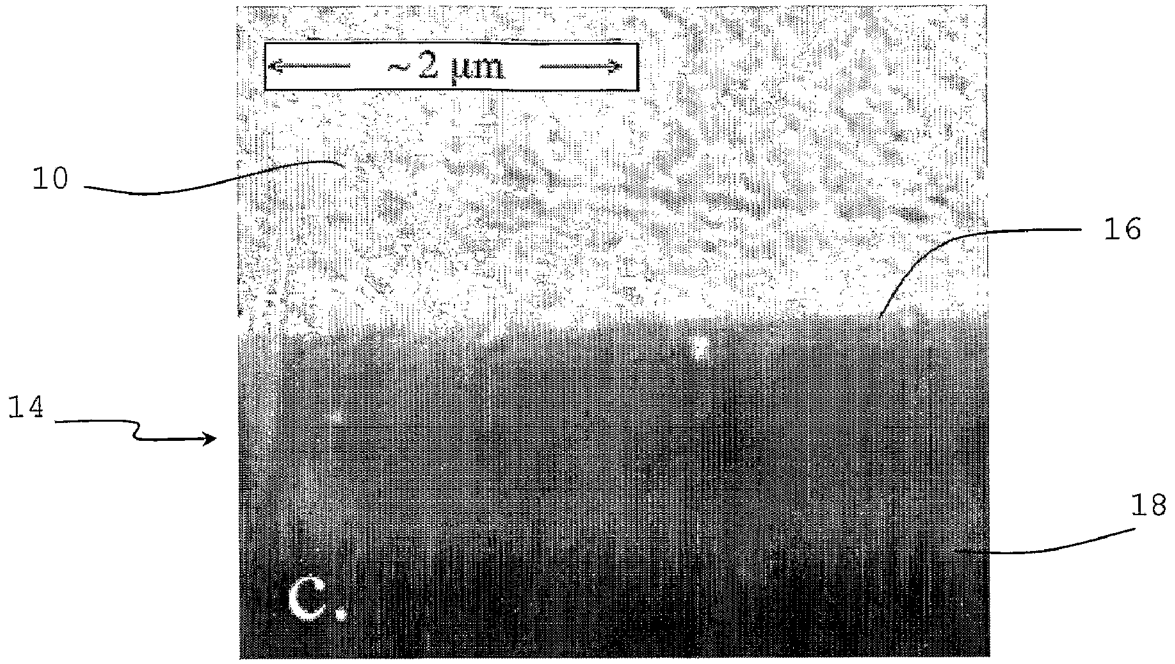
FIG. 3 shows an SEM image of a cleaved nanostructured substrate of the invention.

FIG. 3 shows an SEM image of a cleaved nanostructured substrate of the invention. The substrate 14 is oriented to show a surface 16 and interior 18 thereof. As shown, monodisperse-sized gold nanoparticles 20 are substantially disposed on the surface 16 of the substrate 14. The gold nanoparticles 20 are also shown substantially covering or coating the substrate surface. The substrate 14 and surface 16 shown in FIG. 3 also comprise silicon dioxide.

Figure 4:
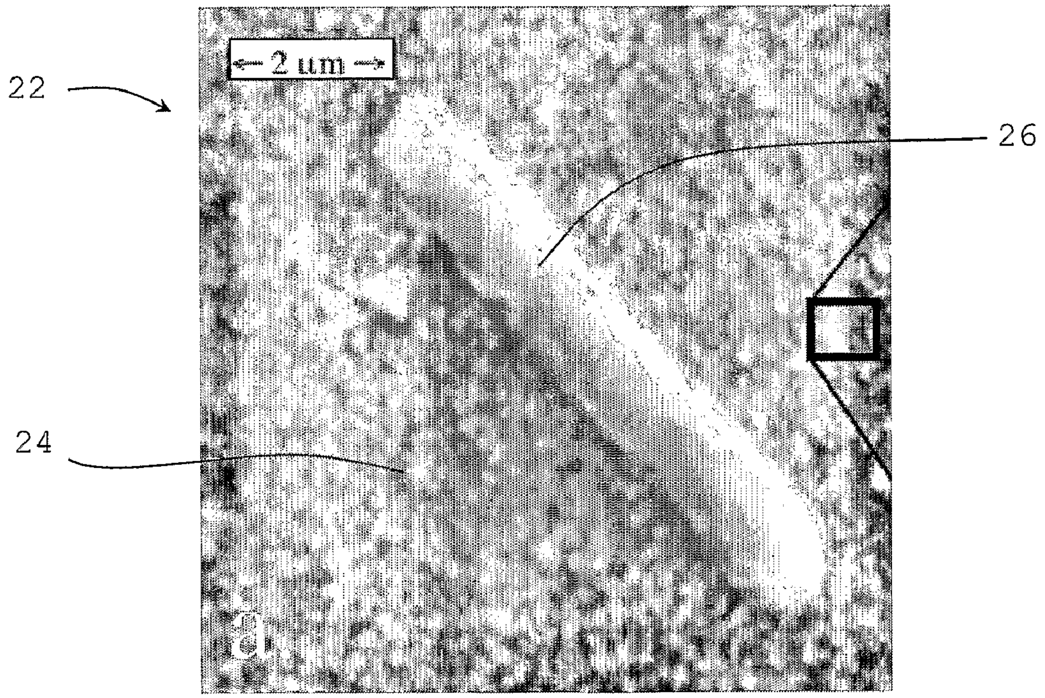
FIG. 4 shows an SEM image of a nanostructured substrate of the invention comprising an entity in contact with substantially monodisperse-sized gold nanoparticles.

In one embodiment, a substrate of the invention comprises an entity substantially disposed on a surface thereof. The substrate surface also comprises monodisperse-sized metal nanoparticles. FIG. 4 shows an SEM image of an exemplary nanostructured substrate of the invention comprising an entity in contact with substantially monodisperse-sized metal nanoparticles. As shown, the substrate 22 comprises monodisperse-sized gold nanoparticles 24. Moreover, the entity 26 in FIG. 4 is a single two-cell chain of *B. anthracis* Sterne disposed on the substrate surface. The entity 26 disposed on the substrate 22 is in contact with one or more of the gold nanoparticles 24.

Exemplary entities for a substrate of the invention can include spores, pathogens, fluids, cells, amino acids, biological materials, molecules, nucleic acids, tissue samples, viruses, bacteria, inorganic materials, serums, vegetative samples, germinating samples, sputum, human blood, bronchoalveolar lavage fluid, cerebral spinal fluid or combinations thereof. In one embodiment, a nanostructured substrate can provide for SERS and spectra therefrom, which are unique to an entity. Preferably, the entity can be in contact with one or more monodisperse-sized metal nanoparticles substantially disposed on the substrate surface.

The examples herein are provided to illustrate advantages of the invention that have not been previously described. The examples are also intended to assist a person of ordinary skill within the art in syntheses and uses of a nanostructured substrate of the invention. The examples can incorporate or otherwise include any variations or inventive embodiments or aspects as described above. The embodiments described above can also incorporate or otherwise include any variations or inventive embodiments or aspects of the examples herein. The examples are also not intended in any way to limit or otherwise narrow the disclosure or scope thereof as generally provided herein.

EXAMPLES

Exemplary Syntheses of Substrates of the Invention

Exemplary syntheses of nanostructured substrates of the invention were performed via in situ growth methods. For example, a gold ion doped sol-gel was formed by hydrolysis of tetramethoxysilane ($Si(OCH_3)_4$) in an acidic (about 0.005 milliliters (ml) of about 1 percent (%), volume per volume, concentration of hydrochloric acid (HCl)) methanol solution (about 10 ml of high performance liquid chromatography (HPLC) grade methanol, about 5 ml of water and about 3 ml of $Si(OCH_3)_4$ 99.99% from Sigma-Aldrich, St. Louis, Mo. 63103) of metal precursors such as chlorauric acid ($HAuCl_4$) (about 50 microliters (μl) of about 1 molar (M) $HAuCl_4$ from Sigma-Aldrich) based metal precursors.

After about 3 hours of agitation to complete hydrolysis, sol-gel aliquots (about 25 μl) within microcentrifuge tubes, such as polypropylene microcentrifuge tubes, were dried in a fume hood for about 12 to 48 hours at ambient temperature and airflow (relative humidity about 40%). The resulting matrixes of gel pellets or chips comprising metal precursors were then exposed to water saturated air for about 1 hour. These gel pellet or chip matrixes were vigorously agitated (about 30 seconds) with about 0.66 millimolar (mM) of a reducing agent such as an aqueous sodium borohydride (99.99% from Sigma-Aldrich) solution in a first reduction step. The first reduction step rapidly reduced the metal precursors in the matrixes providing gold seeds for substantially monodisperse-sized metal nanoparticle surface growth during a second reduction step.

The solution was drained and about 50 ml of water were added to the gel pellet or chip matrixes. Gentle agitation was then induced for about 30 minutes to form silicon dioxide substrates from the matrixes for monodisperse-sized metal nanoparticle growth thereon. For the second reduction step, these substrates remained in a low concentration of a reducing agent for about 24 hours. The second reduction step slowly reduced the metal precursors to grow monodisperse-sized gold nanoparticles substantially on an exposed outer surface of the substrate, yielding an exemplary nanostructured substrate of the invention such as shown in FIG. 3.

To aid in consistent syntheses of nanostructured substrates of the invention, ambient airflow can also be filtered via a hydrocarbon absorbing filter and 300 micron (μ) particulate filters. The exemplary nanostructured substrates of the invention provide for SERS. The invention also contemplates performing exemplary syntheses or variations thereof to yield substantially monodisperse-sized metal nanoparticles other than gold. For example, given syntheses can be varied to produce monodisperse-sized silver nanoparticles substantially disposed on a substrate of the invention by substituting silver nitrate ($AgNO_3$) for $HAuCl_4$, limiting the first reduction step to about 5 seconds and employing about a five-fold lower reducing agent concentration.

Exemplary syntheses of a nanostructured substrate can also be varied by manipulating metal precursor or reducing agent concentrations. Moreover, adjusting relative humidity during syntheses can yield low or high densities of substantially monodisperse-sized metal nanoparticles. For example, a low density of monodisperse-sized metal nanoparticles can partially cover or coat a surface for a nanostructured substrate of the invention. By comparison, a high density of monodisperse-sized metal nanoparticles can substantially or entirely cover or coat a substrate surface. Such variations to exemplary syntheses for a substrate of the invention can also affect Raman cross-sectional enhancement including SERS intensities.

Nanostructured substrates produced by exemplary syntheses can also feature monodisperse-sized metal nanoparticles substantially aggregated in clusters. For example, monodisperse-sized gold nanoparticles were substantially disposed on substrates comprising silicon dioxide, partially covering or coating outer surfaces thereof. In contrast to nanostructured substrates of the invention, conventional surfaces or substrates for SERS consist of metal particles or colloids embedded or dispersed therein.[1] Metal particles embedded within conventional surfaces or substrates also tend to be nonuniformly or inhomogeneously proportioned and sized.[2]

Exemplary Uses of Substrates of the Invention

Exemplary uses for nanostructured substrates include providing for SERS of entities such as bacterial or viral pathogens. A nanostructured substrate can also provide for SERS of chemical or biological molecules. To demonstrate SERS of bacterial pathogens, *E. coli, S. typhimurium, Bacillus cereus* (*B. cereus*), *B. anthracis* Sterne and *B. thuringiensis* samples were obtained from Carolina Biological Supply, Burlington, N.C. 27215. *Bacillus subtilis* (*B. subtilis*) YS11 was also obtained from the *Bacillus* Genetic Stock Center (BGSC), Columbus, Ohio 43210.

In addition, *B. subtilis* 3610 (SSB2) and its congenic insertion deletion construct hag::erm (SSB71) were provided by the Department of Microbiology and Molecular Genetics, Harvard Medical School, Boston, Mass. 02115. A *B. anthracis* Sterne cotE::cat mutant was also provided by the Department of Microbiology and Immunology, Loyola University Medical Center, Chicago, Ill. 60153. The in vitro bacterial pathogen samples were grown in about 5 ml of Luria-Bertani (LB) broth (about 5 hours) to an OD600 equal to about 1. The samples were then washed five times with water and resuspended in about 0.25 ml of water.

A platinum loop was used to place about 1 μl of a bacterial pathogen sample suspension on an nanostructured substrate of the invention. SERS spectra were generally acquired within minutes after placing the samples on the substrate surface comprising substantially monodisperse-sized metal nanoparticles. Bulk Raman spectra of bacterial pathogen samples, excited with about 300 milliwatts (mW) at about 785 nm, were correspondingly placed on a standard potassium bromide (KBr) material. A Renishaw Raman microscope (model RM2000) capable of about 2λ spatial resolution was used for measurements at about 785 nm (diode laser excited).

Typically, SERS spectra of bacterial pathogen samples on a nanostructured substrate of the invention were obtained with an incident laser power at about 1 to 3 mW and spectral acquisition time of about 10 seconds. An exemplary spectral resolution was set to about 3 $cm^{-1}$ for a cooled charged coupled device (CCD) (400×578 array size) detection system (0.25 meter (m) spectrometer fitted with a 1200 groove per millimeter (mm) grating). A 520 $cm^{-1}$ vibrational band of a silicon wafer provided frequency calibration. Several microscope objectives including about 50 and 100 times (×) objectives were used for excitation and collection.

Figure 5:
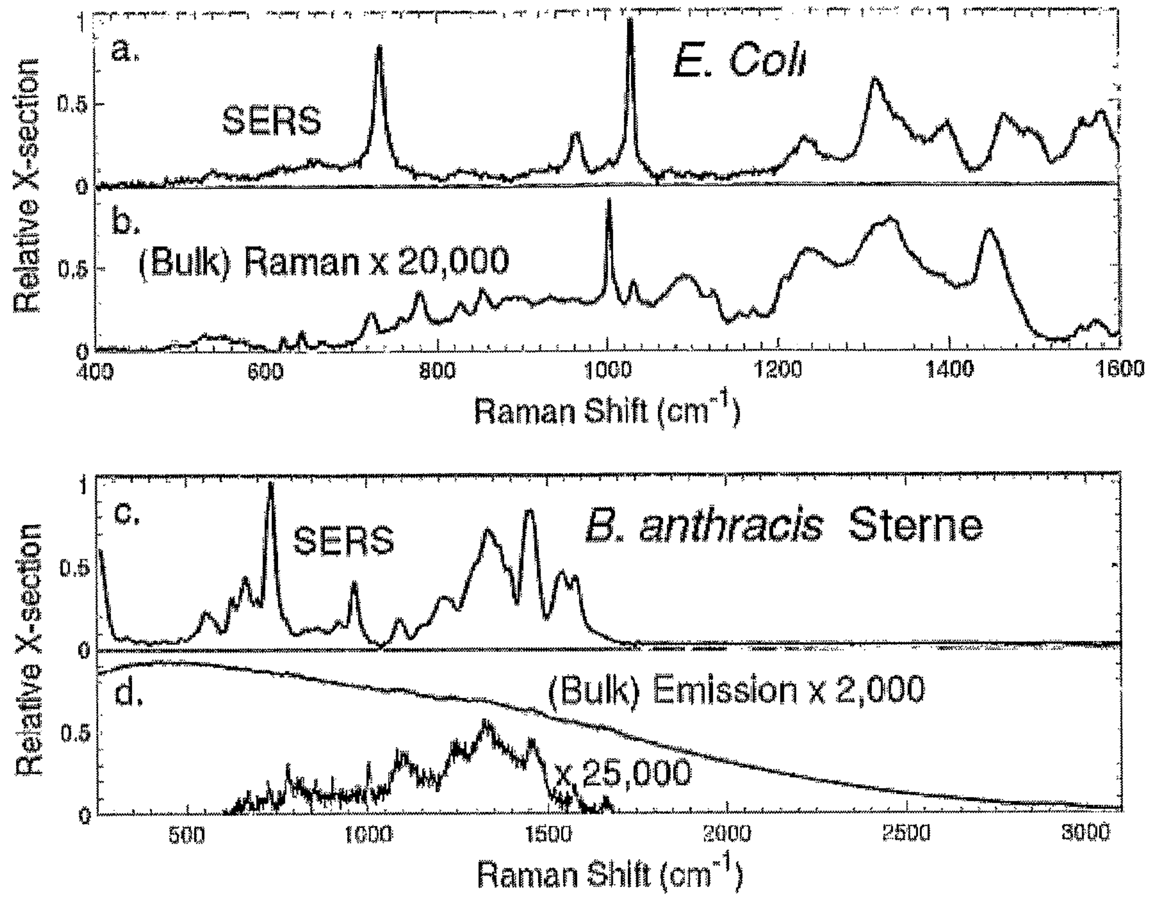
FIG. 5 shows SERS and bulk Raman (non-SERS) spectra for Gram-negative *Escherichia coli* (*E. coli*) and Gram-positive *Bacillus anthracis* Sterne (*B. anthracis* Sterne)

FIG. 5 shows SERS and bulk Raman spectra for Gram-negative *E. coli* and Gram-positive *B. anthracis* Sterne bacteria. The relative scattered power per bacterium of the SERS and bulk Raman spectra of *E. coli* and *B. anthracis* Sterne, normalized for incident laser power, sample concentration and data collection times are shown in FIG. 5. The SERS spectra in FIG. 5 were obtained from monodisperse-size gold nanoparticle covered substrates of the invention. As shown, the spectrum of *E. coli* was amplified by a factor of $2\times10^4$ per bacterium when comparing the intensities of the strongest vibrational band of the SERS and bulk Raman spectra.

Correspondingly, Raman cross-sectional enhancement per *B. anthracis* Sterne bacterium was about $5\times10^4$ due to the gold nanoparticles of the substrate. The greater amplification factor for *B. anthracis* Sterne as compared to *E. coli* may be attributable to different Gram-positive and Gram-negative cell surface structures of these two types of bacterial pathogens. About 300 mW of incident 785 nm excitation power and 100 second signal accumulation times were used to obtain the bulk Raman spectra of FIG. 5. By comparison, the SERS spectra were excited with about 2 mW and collected in about 10 seconds.

The bulk Raman spectrum of *B. anthracis* Sterne excited at 785 nm was dominated by broad fluorescence as shown by spectrum (d) in FIG. 5. A relatively weak and noisy spectrum can also be identified overlapping the broad fluorescence of the bulk Raman *B. anthracis* Sterne emission. In contrast, only a strongly enhanced emission, lacking the broad fluorescence feature, was evident for the SERS spectrum of *B. anthracis* Sterne produced via a nanostructured substrate comprising substantially monodisperse-sized gold nanoparticles disposed on a surface thereof.

Figure 6:
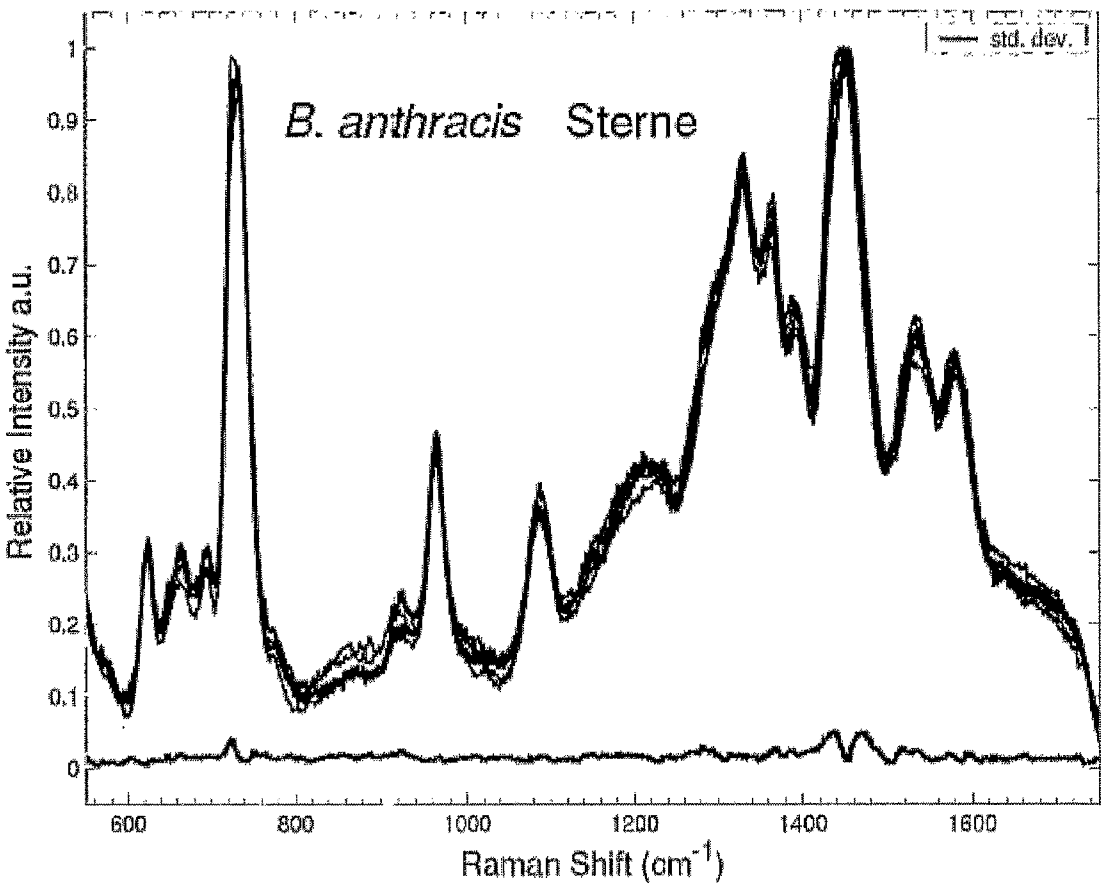
FIG. 6 shows SERS spectra of *B. anthracis* Sterne provided via nanostructured substrates of the invention.

FIG. 6 shows six SERS spectra of *B. anthracis* Sterne obtained from nanostructured substrates of the invention. The spectra were observed at three separate locations on a substrate surface, and from three different substrates of the invention each of which featuring substantially monodisperse-sized gold nanoparticles. Each spectrum was normalized by the intensity of the strongest band thereof. A corresponding standard deviation spectrum is also shown in FIG. 6.

The absolute scattering intensities of these spectra varied by less than about 15% at about 735 $cm^{-1}$ (signal maximum). These spectra were typical of samples from the same *B. anthracis* Sterne culture or cultures grown on different days in a common broth type. The spectra in FIG. 6 demonstrate the reproducibly and reliably of detecting and identifying bacterial pathogens via nanostructured substrates of the invention. By comparison, conventional metal particle embedded surfaces or substrates and colloids dispersed in solution for SERS are often irreproducible and, as a result, unreliable for routinely detecting and identifying such pathogens via SERS.[3]

Figure 7:
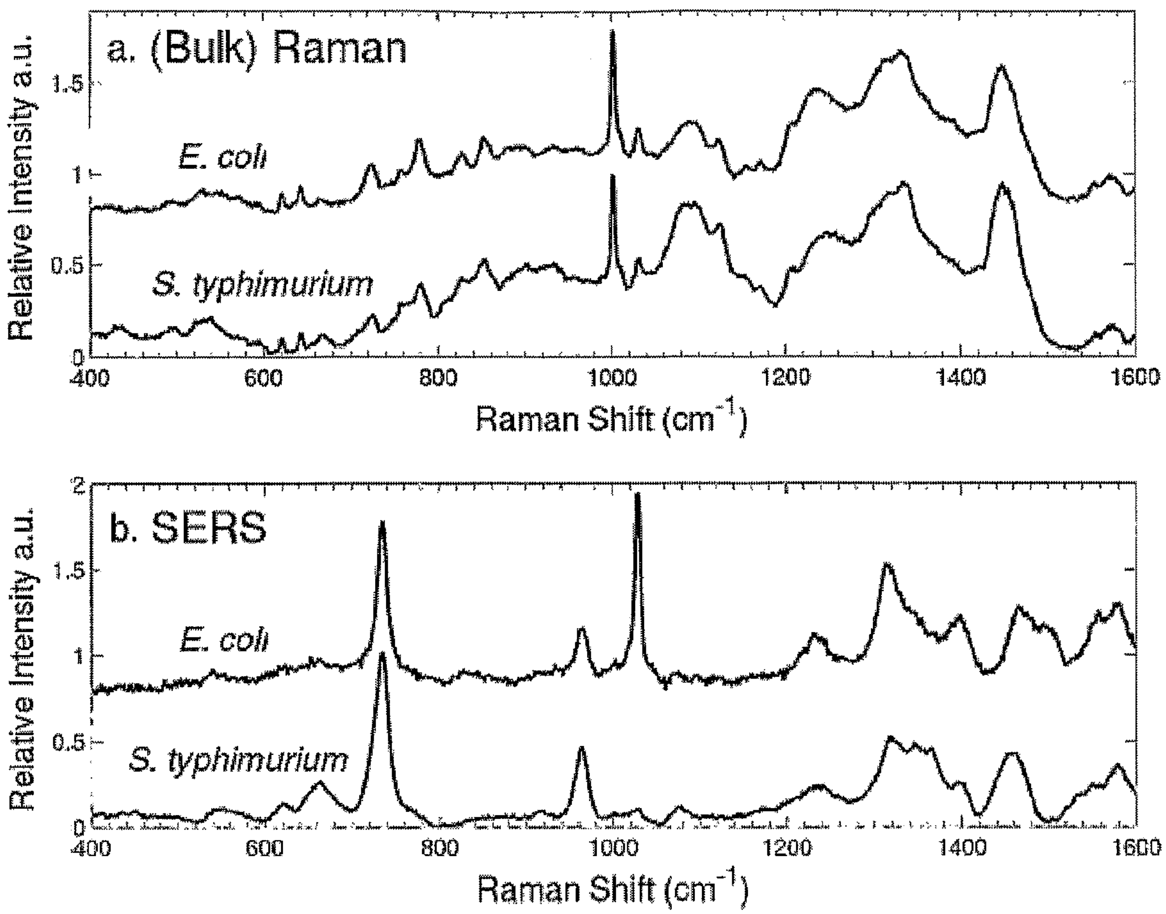
FIG. 7 shows SERS and bulk Raman spectra for *E. coli* and *Salmonella typhimurium* (*S. typhimurium*)

FIG. 7 shows SERS and bulk Raman spectra for two phylogenetically related species, *E. coli* and *S. typhimurium*. As shown, the bulk Raman spectra of these two bacterial pathogens were extremely similar judging by the peak positions and relative intensities of the observed emission bands in spectra (a) of FIG. 7. To contrast, SERS spectra of *E. coli* and *S. typhimurium* on nanostructured substrates of the invention shown by spectra (b) in FIG. 7 exhibited much more distinct vibrational features than the bulk Raman spectra. For example, the relative intensity of a 1050 $cm^{-1}$ band and relative intensity patterns in the 1200 to 1700 $cm^{-1}$ region were obvious spectral differences in the SERS spectra of *E. coli* and *S. typhimurium* obtained from a substrate of the invention. As a result, the greater spectral discrimination observed in the SERS spectra from nanostructured substrates of the invention allow more accurate and faster species detection and identification than conventional Raman or infrared (IR) absorption techniques.

In addition to enhanced species vibrational specificity, the number of transitions in the SERS spectra of *E. coli* and *S. typhimurium* via a substrate of the invention were significantly fewer than in corresponding bulk Raman spectra. FIG. 7 also shows that SERS spectra obtained from a substrate of the invention exhibited reduced vibrational spectral congestion relative to bulk Raman spectra. Such simplified and more species distinct vibrational signatures using a substrate comprising substantially monodisperse-sized metal nanoparticles provides a spectroscopic technique surpassing the capabilities of conventional Raman or IR absorption techniques.

Figure 8:
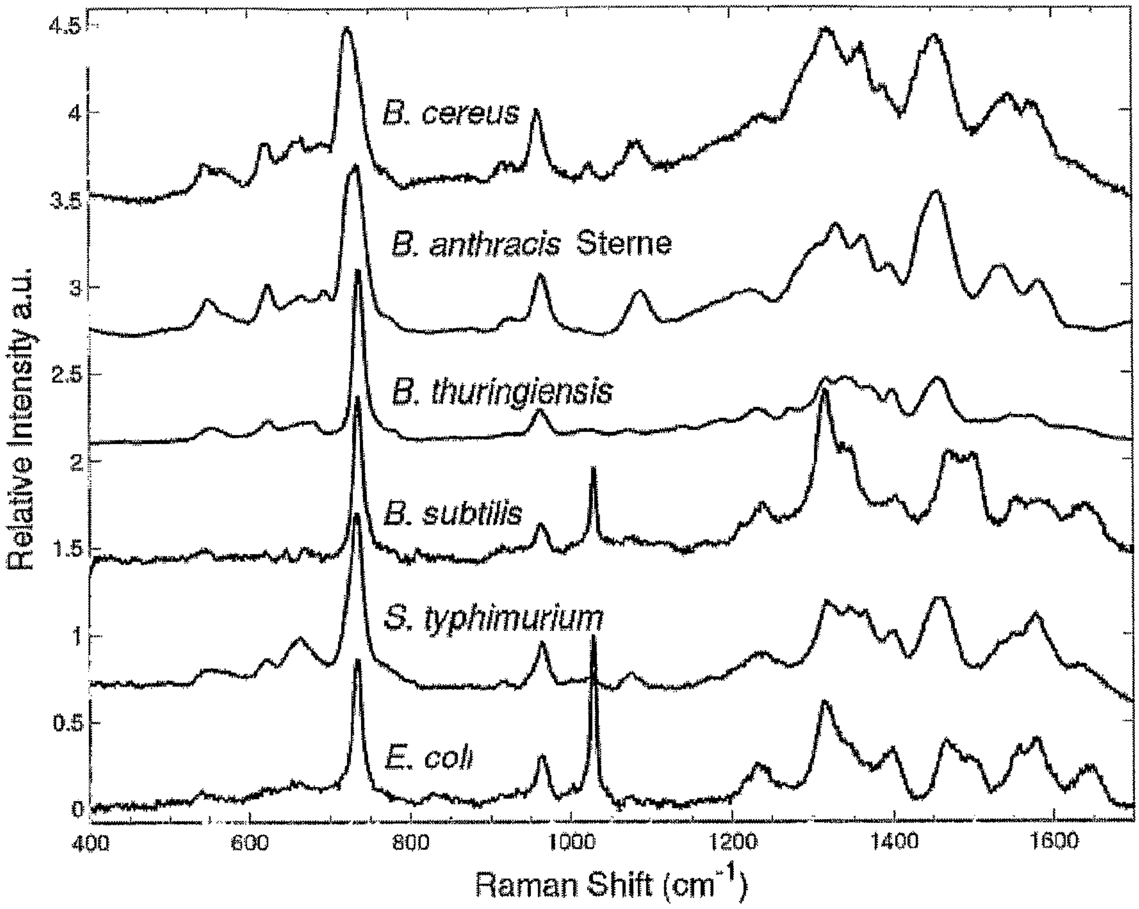
FIG. 8 shows SERS spectra for several bacterial pathogens produced by using a nanostructured substrate of the invention.

FIG. 8 shows SERS spectra for several bacterial pathogens yielded from a nanostructured substrate of the invention. These spectra resulted from the scattering of about 25 to 100 vegetative bacterial cells, depending on the bacterial pathogen, illuminated by about 2 mW of incident 785 nm laser power for an accumulation time of about 10 seconds. The spectra were corrected for the spectral response of the system and some baseline effects. Additional averaging or smoothing was not applied to the spectra. The spectra of FIG. 8 demonstrated that SERS spectra produced via a nanostructured substrate of the invention can display excellent signal to noise for vegetative bacterial cells excited by low laser power radiation at about 785 nm.

Additionally, the spectra of FIG. 8 demonstrated that SERS spectra produced via a nanostructured substrate of the invention can provide reproducible and reliable vibrational signatures specific to a bacterial pathogen. The invention also contemplates obtaining vibrational signatures for any suitable entity using a substrate comprising substantially monodisperse-sized metal nanoparticles. In one embodiment, these signatures can comprise a vibrational signature library for reproducible and reliable entity detection or identification.

For example, a vibrational signature library of the invention can be maintained on a system comprising a processor such as computer. Such a computer can also comprise algorithms or instructions that are stored in memory and executed by the processor for the detection or identification of an entity by using a substrate of the invention for SERS. The invention also contemplates that exemplary algorithms or instructions can be performed by a processor executing scripts, compiled programs or any other suitable components such as downloadable applets or plug-ins. Furthermore, a vibrational signature library can be stored on firmware, hardware, software or combinations thereof such as combinatorial logic, integrated circuits or gate arrays.

Using a nanostructured substrate of the invention for SERS, bacterial pathogen strains and mutants can also be distinguished based on unique vibrational signatures. For example, SERS spectra for a *B. subtilis* congenic mutant lacking flagella hag::erm and *B. subtilis* strains, YS11 and 3610, exhibited distinct vibrational signatures using a nanostructured substrate of the invention. These spectra demonstrated that a nanostructured substrate can provide a reproducible and reliable basis for detection or identification of closely related species of bacterial pathogens.

Figure 9:
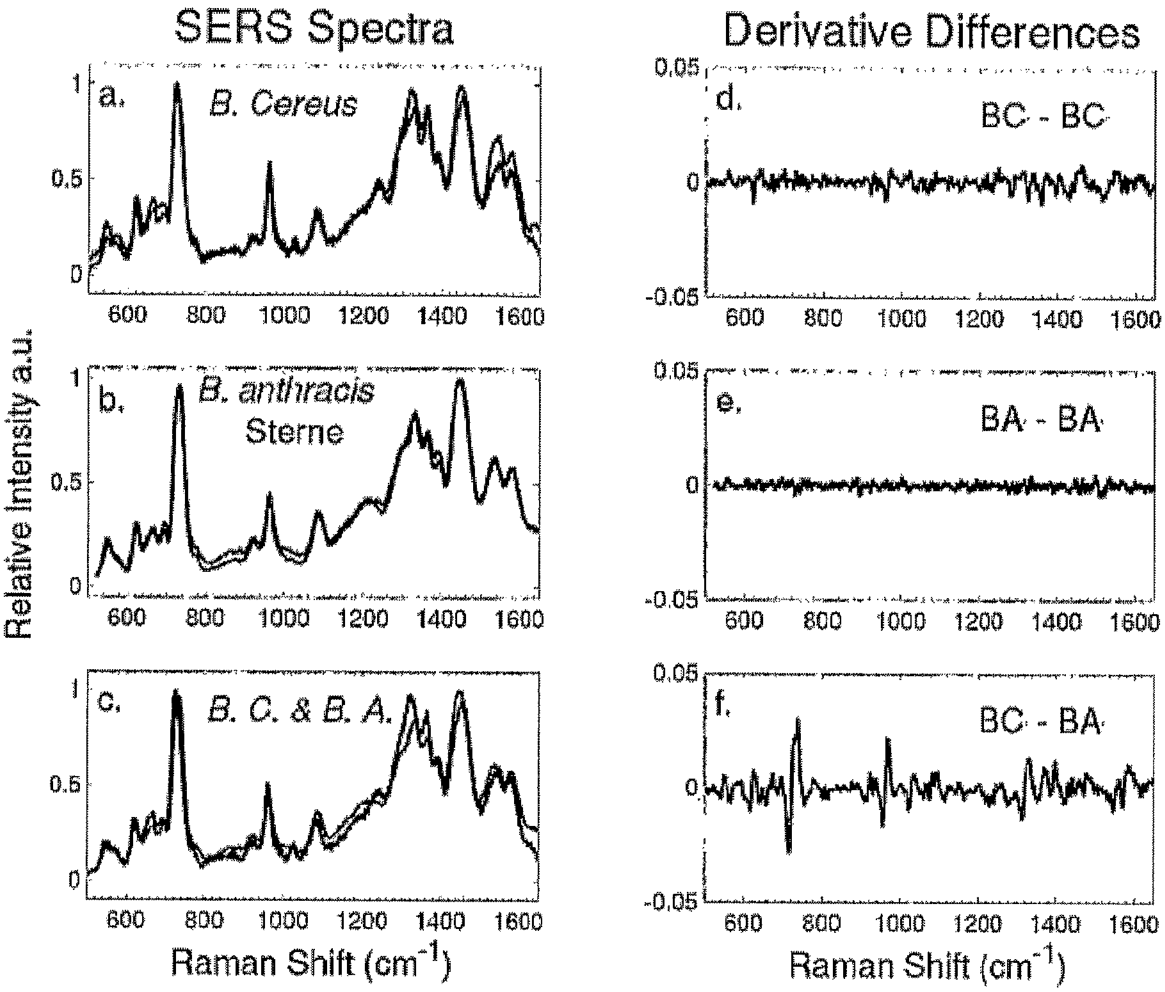
FIG. 9 shows SERS spectra for two closely related species of bacterial pathogens obtained via a nanostructured substrate of the invention.

Additional evidence for the ability of a nanostructured substrate of the invention to provide species specific vibrational signatures for detection and identification of bacterial pathogens is demonstrated by FIG. 9. FIG. 9 shows SERS spectra for two very closely related bacterial pathogen species, *B. cereus* and *B. anthracis* Sterne, produced by using a substantially monodisperse-sized gold nanoparticle covered substrate of the invention. These spectra are shown as spectra (a), (b) and (c). Moreover, derivative difference spectra of *B. cereus* and *B. anthracis* Sterne, spectra (d) and (e) of FIG. 9, demonstrated signal reproducibility achievable via nanostructured substrates of the invention. The derivative difference spectrum between *B. cereus* and *B. anthracis* Sterne, spectrum (f) of FIG. 9, also demonstrated the ability of SERS spectra from substrates of the invention to provide distinct spectral distinctions between two species that can be used for detection and identification purposes. The invention also contemplates alternative uses for a substrate comprising monodisperse-sized metal nanoparticles based on these species specific SERS spectra.

Figure 10:
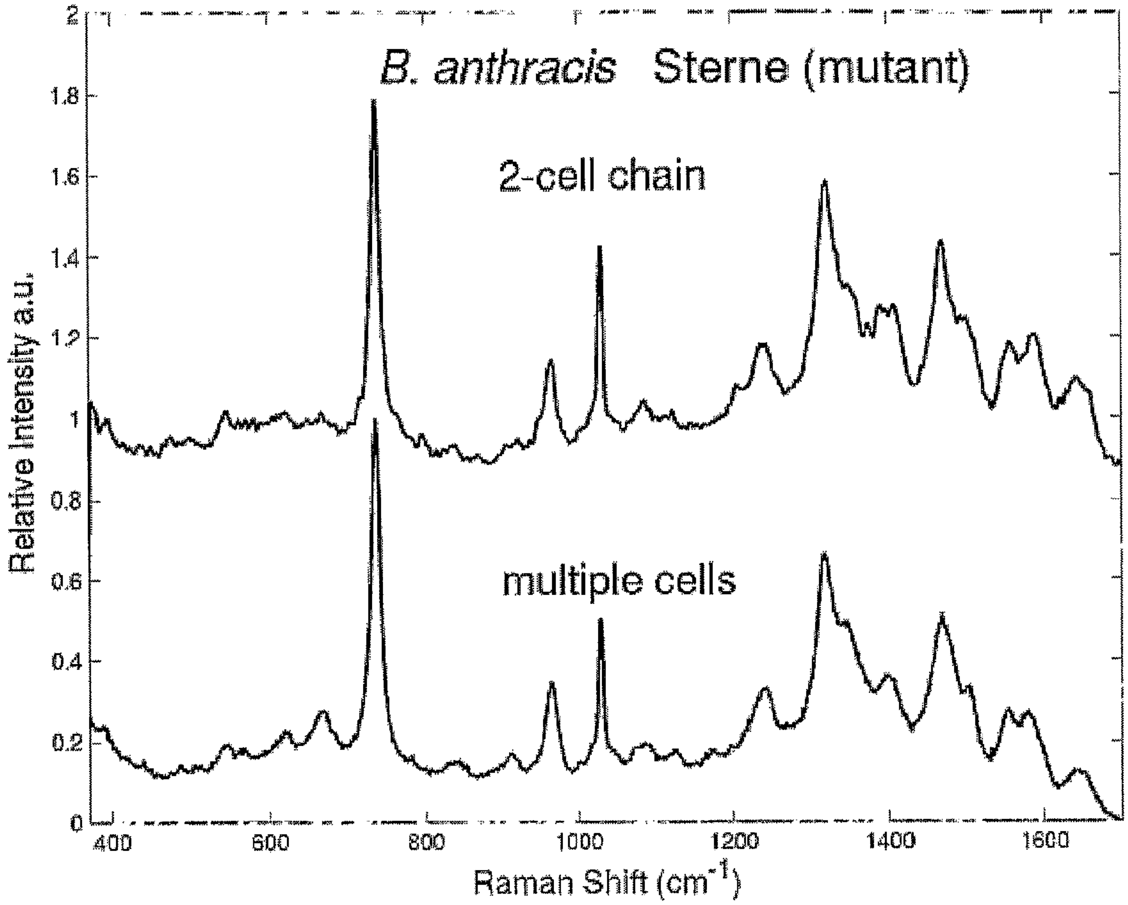
FIG. 10 shows a SERS spectrum of a two-cell chain of *B. anthracis* Sterne compared to a SERS spectrum resulting from multiple cells yielded via a nanostructured substrate of the invention.

As an example of single cell capability for a substrate of the invention, SERS spectrum of a *B. anthracis* Sterne (cotE::cat) mutant two-cell chain was detected and identified. In particular, FIG. 10 shows a SERS spectrum of a two-cell chain of *B. anthracis* Sterne compared to a SERS spectrum resulting from multiple cells yielded via a nanostructured substrate of the invention comprising monodisperse-sized gold nanoparticles. A white light image at the laser focal region confirmed that only a single bacterium was in the illuminated volume during detection and identification. A 100× objective and 20 seconds of 3 mW of 785 nm incident laser power were used to observe the single cell level spectrum of FIG. 10.

The SERS spectrum of multiple *B. anthracis* cells (about 30 cells) was also obtained with less tightly focused excitation (50× objective and about 10 seconds for data accumulation). In addition to enabling bacterial pathogen mixture identification, single cell detection capabilities for a substrate of the invention can minimize the effects of spectral contamination in the SERS of biological fluids such as a fluid comprising an entity of interest. Moreover, spectral contributions from non-bacterial components of in vivo derived samples can be greatly reduced as a result of the ability to observe vibrational signatures from a bacterium filled sampling volume.

Figure 11:
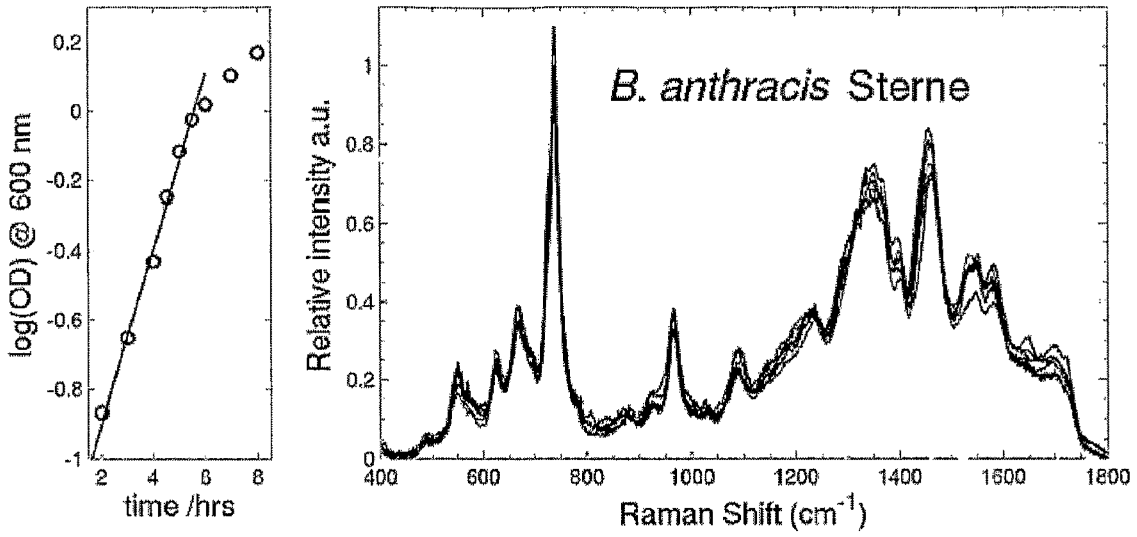
FIG. 11 shows SERS spectra as a function of growth time for *B. anthracis* Sterne cells obtained from a nanostructured substrate of the invention.

FIG. 11 shows SERS spectra for *B. anthracis* Sterne cells obtained from a nanostructured substrate of the invention acquired for cells harvested seven times during the course of bacterial culture growth. The spectra from each of these times through the growth cycle were demonstrated to be nearly identical to one another. By using a nanostructured substrate of the invention for SERS and spectra therefrom, only minimal surface changes were detectable in the life cycle of the culture.

Figure 12:
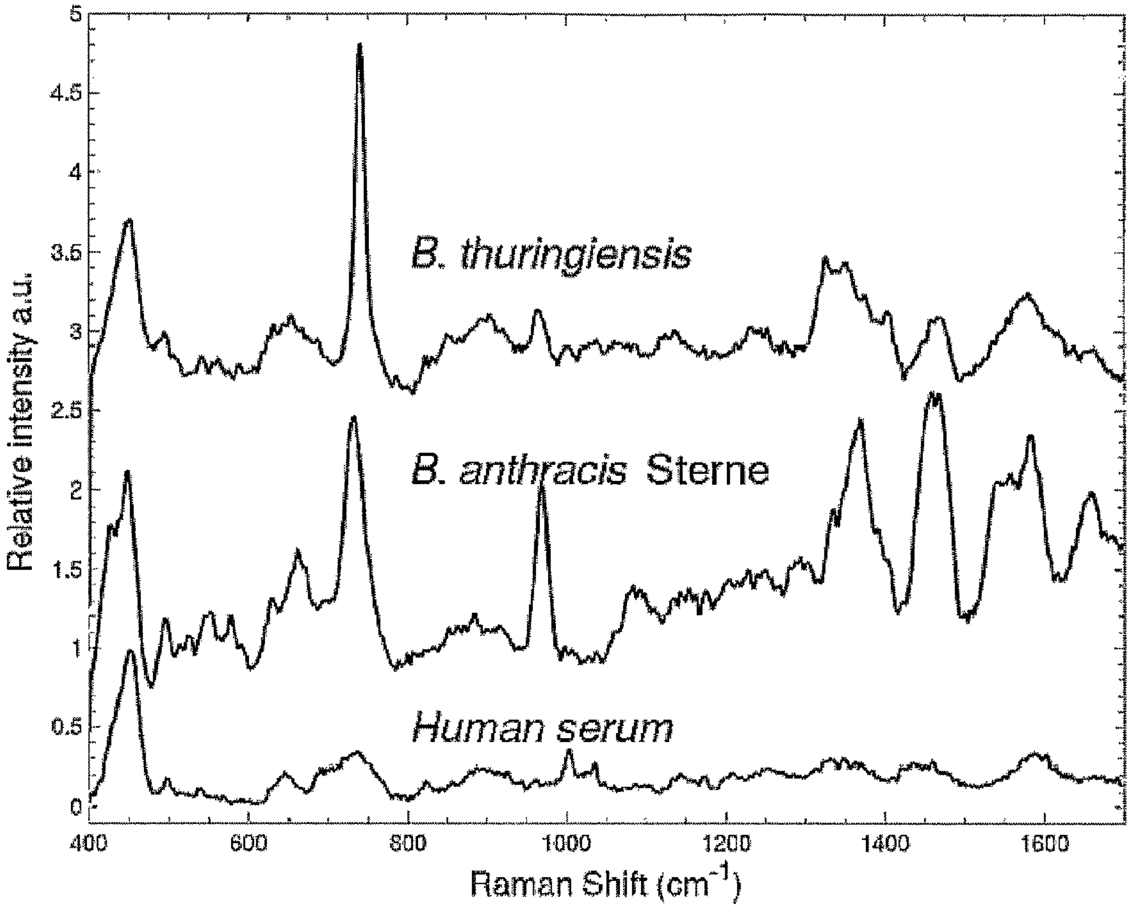
FIG. 12 shows SERS spectra for *Bacillus thuringiensis* (*B. thuringiensis*) and *B. anthracis* Sterne after admixing with human heparinized serum provided via a nanostructured substrate of the invention.

FIG. 12 shows SERS spectra for LB broth cultured *B. thuringiensis* and *B. anthracis* Sterne after admixing with human heparinized serum for about 1 to 3 hours. The admixtures were then placed on a substrate of the invention without additional washing. As shown, high quality vibrational signatures of these bacterial pathogens were obtained in the biological fluid. Although the effects of human heparinized serum on the vibrational signature of *B. anthracis* Sterne and *B. thuringiensis* were observable, reproducible species specific SERS spectral vibrational signatures were still obtained on the nanostructured substrate of the invention.

Figure 13:
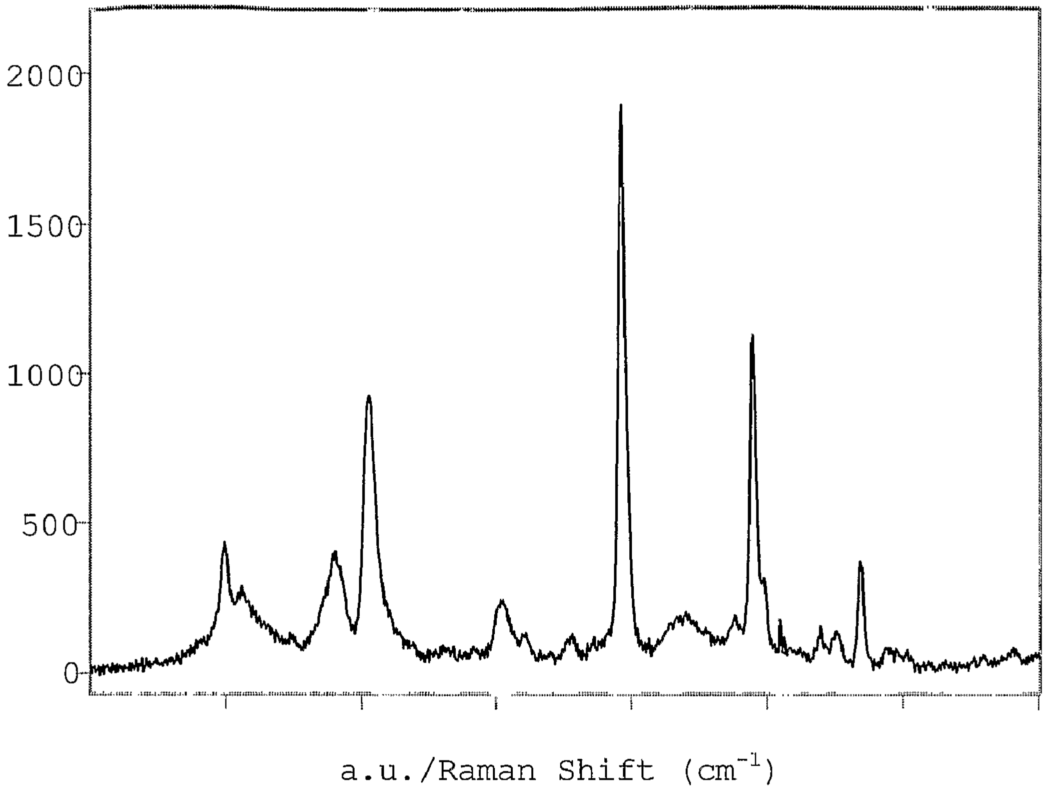
FIG. 13(*a*) shows SERS spectra for *B. subtilis* spores produced by using a nanostructured substrate of the invention.
Figure 13:
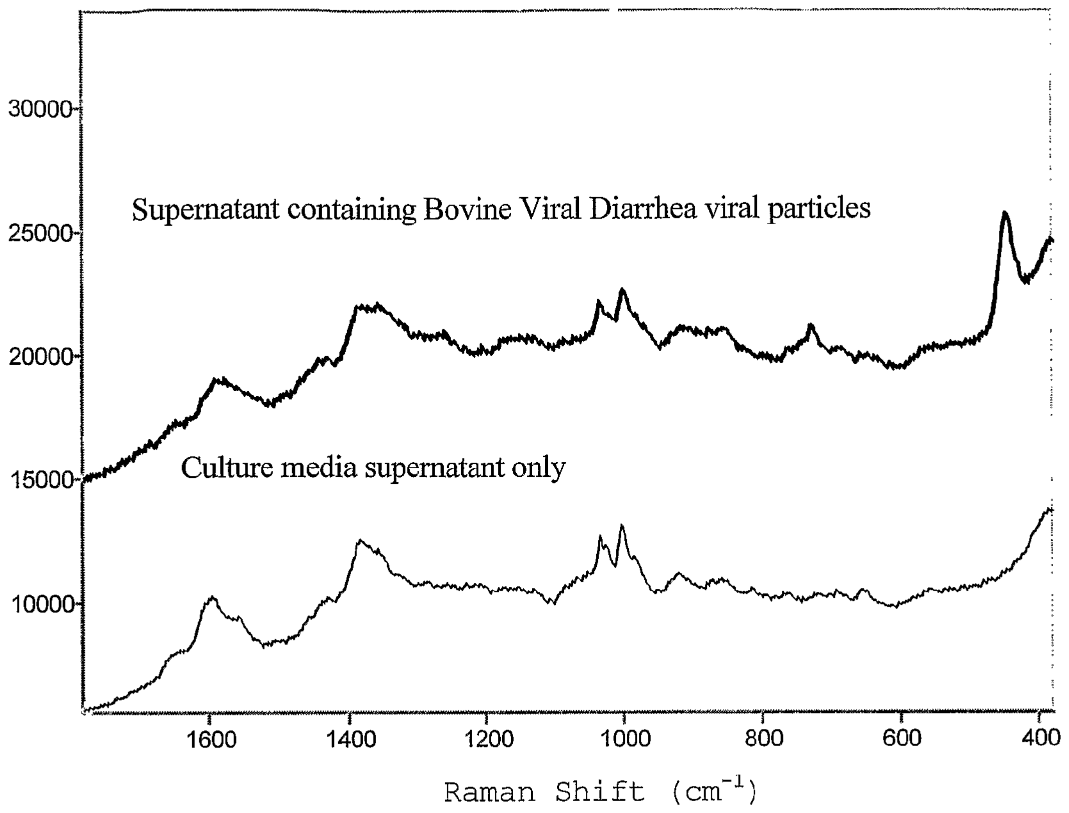

FIG. 13(*a*) shows SERS spectra for *B. subtilis* spores provided via a nanostructured substrate of the invention. An aqueous suspension of *B. subtilis* spores were placed on the substrate. The substrate comprised a surface featuring substantially monodisperse-sized silver nanoparticles. The SERS spectra of these spores were readily observed in about 20 seconds with about 2 mW of 785 nm excitation.

FIG. 13(*b*) shows SERS spectra of the supernatant from culture medium containing bovine viral diarrhea virus particles (upper trace) and a SERS spectrum for the corresponding culture medium supernatant of non-infected cells (lower trace) produced by using a nanostructured substrate of the invention. The nanostructured substrate comprising a surface featuring substantially monodisperse-sized gold nanoparticles. The differences between the upper and lower trace in FIG. 13(*b*) are due to the viral pathogen.

While the invention has been described herein in conjunction with a preferred embodiment, a person of ordinary skill within the art, in view of the foregoing, can effect changes, substitutions of equivalents and other types of alterations to the nanostructured substrates for SERS set forth herein. Each embodiment described above can also have incorporated or otherwise included therewith such variations as disclosed in regard to any or all other embodiments. Thus, it is intended that protection granted by Letter Patent hereon be limited in breadth and scope only by definitions contained in the appended claims and any equivalents thereof.

REFERENCES

1. Olson et al., Characterization of silane-modified immobilized gold colloids as a substrate for surface-enhanced Raman spectroscopy, Anal. Chem., 2001, 73: pp. 4268-4276; Lee et al., Surface-enhanced Raman sensor for trace chemical detection in water, Proc. SPIE, 1999, 3857: pp. 76-84; Creighton et al., Metal colloids, in Surface enhanced Raman Scattering, 1982, Plenum: NYC, pp. 315-337; Volkan et al., A new surface-enhanced Raman scattering substrate based on silver nanoparticles in sol-gel, J. Raman Spect., 1999, 30: pp. 1057-1065; Premasiri et al., Determination of cyanide in waste water by low resolution surface enhanced Raman spectroscopy on sol-gel substrates, J. Raman Spect., 2001, 32: p. 919-922; Garcia-Rodriguez et al., Sol-gel $SiO_2$ films containing colloidal copper particles for surface enhanced Raman scattering of graphite, J. Raman Spect., 1998, 29: pp. 763-771; Akbarain et al., Porous sol-gel silicates containing gold particles as matrixes for surface-enhanced Raman spectroscopy, J. Raman Spect., 1996, 27: pp. 775-783; Lee et al., Silver-doped sol-gel films as the substrate for surface-enhanced Raman scattering, J. Raman Spect., 1997, 30: pp. 635-639; and Farquharson et al., Detection of bioagent signatures: A comparison of electrolytic and metal-doped sol-gel surface enhanced Raman media, Proc. SPIE, 2002, 4575: pp. 62-72.
2. Lee et al., Surface-enhanced Raman sensor for trace chemical detection in water, Proc. SPIE, 1999, 3857: pp. 76-84; Volkan et al., A new surface-enhanced Raman scattering substrate based on silver nanoparticles in sol-gel, J. Raman Spect., 1999, 30: pp. 1057-1065; Premasiri et al., Determination of cyanide in waste water by low resolution surface enhanced Raman spectroscopy on sol-gel substrates, J. Raman Spect., 2001, 32: p. 919; Garcia-Rodriguez et al., Sol-gel $SiO_2$ films containing colloidal copper particles for surface enhanced Raman scattering of graphite, J. Raman Spect., 1998, 29: pp. 763-771; Akbarain et al., Porous sol-gel silicates containing gold particles as matrixes for surface-enhanced Raman spectroscopy, J. Raman Spect., 1996, 27: pp. 775-783; Lee et al., Silver-doped sol-gel films as the substrate for surface-enhanced Raman scattering, J. Raman Spect., 1997, 30: pp. 635-639; and Farquharson et al., Detection of bioagent signatures: A comparison of electrolytic and metal-doped sol-gel surface enhanced Raman media, Proc. SPIE, 2002, 4575: pp. 62-72.
3. Lee et al., Surface-enhanced Raman sensor for trace chemical detection in water, Proc. SPIE, 1999, 3857: pp. 76-84; Volkan et al., A new surface-enhanced Raman scattering substrate based on silver nanoparticles in sol-gel, J. Raman Spect., 1999, 30: pp. 1057-1065; Premasiri et al., Determination of cyanide in waste water by low resolution surface enhanced Raman spectroscopy on sol-gel substrates, J. Raman Spect., 2001, 32: p. 919; Garcia-Rodriguez et al., Sol-gel $SiO_2$ films containing colloidal copper particles for surface enhanced Raman scattering of graphite, J. Raman Spect., 1998, 29: pp. 763-771; and Akbarain et al., Porous sol-gel silicates containing gold particles as matrixes for surface-enhanced Raman spectroscopy, J. Raman Spect., 1996, 27: pp. 775-783.

What is claimed is:

1. A method for synthesis of a nanostructured substrate for SERS, the method comprising:

hydrolyzing a solution comprising metal precursors;

reducing a quantity of the metal precursors into a matrix in a first reduction;

adding an aqueous solution to the reduced matrix to form the substrate therefrom; and growing substantially monodisperse-sized metal nanoparticles on an outer surface of the substrate in a second reduction that reduces the metal precursors in the aqueous solution.

2. The method of claim 1, wherein the substantially monodisperse-sized metal nanoparticles comprise silver, copper, gold or combinations thereof.

3. The method of claim 1, wherein the surface of the substrate comprises silicon, silicon dioxide, aluminum, titanium or combinations thereof.

4. The method of claim 1, wherein the metal nanoparticles are substantially aggregated in clusters.

5. The method of claim 4, wherein clusters comprise from about 2 to 25 metal nanoparticles.

6. The method of claim 1, wherein the metal nanoparticles are substantially spheroidal.

7. The method of claim 6, wherein the metal nanoparticles have diameters in the range from about 40 to 120 nm.

8. The method of claim 1 further comprising agitating the solution during hydrolysis.

9. The method of claim 1 further comprising air-drying the hydrolyzed solution to form the matrix and exposing said matrix to a water-saturated air.

10. The method of claim 1, wherein reducing the metal precursors in the first reduction provides metal seeds that grow the substantially monodisperse-sized metal nanoparticles on the outer surface of the substrate during the second reduction.

11. The method of claim 1 further comprising agitating the aqueous solution and reduced matrix when adding said aqueous solution to said reduced matrix.

12. The method of claim 1, wherein reducing includes adding a reducing agent.

13. The method of claim 12 further comprising selectively adjusting a concentration of the reducing agent.

14. The method of claim 1, wherein the solution comprising metal precursors is selected from the group consisting of: a methanol solution having chlorauric acid metal precursors, and a methanol solution having silver nitrate metal precursors.

15. The method of claim 1, wherein growing substantially monodisperse-sized metal nanoparticles on the outer surface of the substrate produces electrostatic attraction between the substantially monodisperse-sized metal nanoparticles and molecules in said substrate.

16. A nanostructured substrate for SERS, the substrate produced by the method of claim 1.

17. A method for detecting or identifying an entity using a nanostructured substrate, the method comprising:

hydrolyzing a solution comprising metal precursors;

reducing a quantity of the metal precursors into a matrix in a first reduction;

adding an aqueous solution to the matrix of the first reduction to form the substrate therefrom;

growing substantially monodisperse-sized metal nanoparticles on an outer surface of the substrate in a second reduction that reduces the metal precursors in the aqueous solution;

disposing the entity on the outer surface of the substrate; and detecting or identifying the entity using a spectrum of said entity on said substrate.

18. The method of claim 17 further comprising providing a vibrational signature of the entity.

19. The method of claim 17 wherein disposing the entity includes disposing said entity to be in contact with at least one of the substantially monodisperse-sized metal nanoparticles grown on the outer surface of the substrate.

* * * * *